United States Patent [19]

Pestellini et al.

[11] Patent Number: 4,503,075

[45] Date of Patent: Mar. 5, 1985

[54] DERIVATIVES OF 1-ALKYLAMINE-3[4(P-ALKYLOXY-BENZAMIDE)PHENOXY]-2-PROPANOL, HAVING BETA-SYMPATHOLYTIC ACTIVITY, THEIR SALTS, AND PRODUCTION PROCESSES THEREOF

[75] Inventors: Vittorio Pestellini; Mario Ghelardoni, both of Florence; Danilo Giannotti, Altopascio; Alessandro Giolitti, Florence; Carlo A. Maggi, Florence; Stefano Manzini, Florence; Guglielmo Grimaldi, Florence; Alberto Meli, Florence, all of Italy

[73] Assignee: A. Menarini S.A.S., Italy

[21] Appl. No.: 441,101

[22] Filed: Nov. 12, 1982

[51] Int. Cl.$^3$ .................. C07C 103/82; A61K 31/165
[52] U.S. Cl. .................................. 514/622; 564/174; 564/179
[58] Field of Search .................. 564/174, 176, 179; 424/324

[56]  References Cited

U.S. PATENT DOCUMENTS

| | | | |
|---|---|---|---|
| 3,481,980 | 12/1969 | Teitel et al. .................. | 564/176 |
| 3,676,493 | 7/1972 | Smith .......................... | 564/176 X |
| 3,852,468 | 12/1974 | Howe et al. .................. | 564/157 X |
| 3,898,278 | 8/1975 | Ghelardoni et al. .......... | 564/179 X |
| 4,014,920 | 3/1977 | Jaeggi et al. ................. | 564/157 X |
| 4,072,760 | 2/1978 | Hedegaard .................... | 564/179 X |

*Primary Examiner*—Thomas A. Waltz
*Attorney, Agent, or Firm*—McGlew and Tuttle

[57] ABSTRACT

The invention comprises: a derivative of 1-alkylamine-3-[4(p-alkyloxy-benzamide)phenoxy]-2-propanol of general formula I:

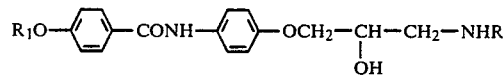

where $R_1$ is a linear or branched alkyl chain with 1 to 8 carbon atoms included, an alkenyl chain with 2 to 8 carbon atoms included, or an arylalkyl chain with 7 to 10 carbon atoms included, and R is a linear or branched alkyl group with 1 to 8 carbon atoms included;
a compound as above, in an optically active form;
pharmaceutically acceptable, non toxic salts of the above compounds;
synthesis processes for obtaining the above compounds; and
a pharmaceutical composition based on a compound as defined above.

20 Claims, No Drawings

DERIVATIVES OF 1-ALKYLAMINE-3[4(P-ALKYLOXY-BENZAMIDE)-PHENOXY]-2-PROPANOL, HAVING BETA-SYMPATHOLYTIC ACTIVITY, THEIR SALTS, AND PRODUCTION PROCESSES THEREOF

The invention relates to new derivatives of 1-alkylamine-3[4(p-alkyloxybenzamide)phenoxy]2-propanol, to pharmaceutical compositions containing said products, and to methods for producing and utilizing these 1-alkylamine-3[4(p-alkyloxybenzamide)phenoxy]2-propanol derivatives.

The main object of this invention is to provide a new group of compounds which present sympatholytic activity and can be used in the therapy of troubles or difficulties or effects induced by hyperactivity of the sympathetic nervous system.

It is well known that many derivatives of 1-alkylamine-3-phenoxy-2-propanol present beta-sympatholytic activity, but it is also known that these compounds are lacking in cardioselectivity while showing intensive liver metabolism and cardiac failure risk. Those products, as for example the 1-(p-acetamide-phenoxy)-3-isopropylamine-2-propanol (A. F. Crowther, R. Howe and L. H. Smith, J. Med. Chem. 14, 6, 511, 1971), which present $\beta_1$-cardioselectivity and poor liver metabolism, show, however, no chronotropic selectivity relative to the inotropism. On the contrary, compounds presenting chronotropic selectivity such as, for example, the 1-isopropyl-amine-3-[(2-methylindol-4-yl)oxy]-2-propanol (Swiss Pat. No. 469,002), and the (1-tert.butylamine-ethyl)-2,5-dimethoxybenzylalcohol (Levy, J. Pharmacol. Exp. Ther. 151, 413, 1966; Wilkenfels and Levy, Arch. Int. Pharmacodyn.Ther. 176, 218, 1968), have either no cardioselectivity or are more active on $\beta_2$ receptors than on $\beta_1$ receptors.

The present invention relates to new compounds having an improved beta-sympatholytic activity, of general formula I:

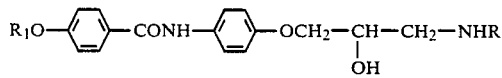

where $R_1$ is a linear or branched alkyl chain with 1 to 8 carbon atoms included, an alkenyl chain with 2 to 8 carbon atoms included, an arylalkyl chain with 7 to 10 carbon atoms included; and R is a linear or branched alkyl group with 1 to 8 carbon atoms included.

It has been found that the new compounds of general formula I and the salts thereof are medicines which present improved $\beta$-sympatholytic activity in that, besides having relevant $\beta_1$-cardioselectivity, intrinsic sympathicomimetic activity and high biodisposability, they show also a high chronotropic selectivity.

Non-limitative examples of compounds according to the general formula I and included in the present invention are:

(1) 1-isopropylamine-3-[4(p-methoxybenzamide)-phenoxy]-2-propanol
(Form.I R=CH(CH$_3$)$_2$ R$_1$=4-OCH$_3$).
m.p. 174°–176° C. (Hydrochloride m.p. 192°–94° C.).
I.R. (nujol) $\nu$ (cm$^{-1}$): 1640 (CO).
H-NMR(DMSO) $\delta$ (p.p.m.): 1.15(d,2xCH$_3$), 2.7–3.0(m,CH$_2$+CH), 3.8–4.1(m,CH$_2$+CH), 6.9–8.3 (m, 2xC$_6$H$_4$).

(2) 1-t-butylamine-3-[4(p-methoxybenzamide)-phenoxy]-2-propanol hydrochloride
Form.I R=C(CH$_3$)$_3$.HCl R$_1$=4OCH$_3$).
m.p. 210°–212° C.
I.R. (nujol) $\nu$ (cm$^{-1}$): 1650 (CO).
H-NMR(D$_2$O) $\delta$ (p.p.m.): 1.30(s,3xCH$_3$) 2.8–3.2(m, CH$_2$+CH) 3.5(s, CH$_3$) 3.7–4.4(m,CH$_2$+CH) 6.5–7.6(m, 2xC$_6$H$_4$).

(3) 1[4(p-ethoxybenzamide)phenoxy]-3-isopropylamine-2-propanol hydrochloride
(Form.I R=CH(CH$_3$)$_2$.HCl R$_1$=4-OC$_2$H$_5$).
m.p. 215°–217° C.
I.R. (nujol) $\nu$ (cm$^{-1}$): 1640 (CO).
H-NMR(DMSO) $\delta$ (p.p.m.): 1.15(d, 2xCH$_3$) 1.25(t,CH$_3$) 2.8–3.6(m,CH$_2$+CH) 3.8–4.3 (m, 2xCH$_2$+CH)6.8–8.0(m,2xC$_6$H$_4$)10.0(s,NH).

(4) 1[4(p-allyloxybenzamide)phenoxy]-3-isopropylamine-2-propanol hydrochloride.
(Form.I R=CH(CH$_3$)$_2$.HCl R$_1$=4-OCH$_2$CH=CH$_2$).
m.p. 200°–202° C.
I.R. (nujol) $\nu$ (cm$^{-1}$): 1635 (CO).

(5) 1-isopropylamine-3-[4(p-propyloxy-benzamide)-phenoxy]-2-propanol hydrochloride
(Form.I R=CH(CH$_3$)$_2$.HCl R$_1$=4-OC$_3$H$_7$).
m.p. 224°–225° C.
I.R. (nujol) $\nu$ (cm$^{-1}$): 1635 (CO).
H-NMR(DMSO) $\delta$ (p.p.m.): 0.95(t,CH$_3$)1.25(d,2xCH$_3$) 1.75(s,CH$_2$)2.8–3.4(m,CH$_2$+CH) 3.7–4.4(m,CH$_2$+CH) 4(t,CH$_2$) 6.8–8.1(m,2xC$_6$H$_4$) 10.1(s,NH).

(6) 1-isopropylamine-3-[4(p-isopropyloxybenzamide)phenoxy]-2-propanol hydrochloride
(Form.I R=CH(CH$_3$)$_2$ R$_1$=4OCH(CH$_3$)$_2$).
m.p. 218°–219° C.
I.R. (nujol) $\nu$ (cm$^{-1}$): 1635 (CO)
H-NMR(DMSO) $\delta$ (p.p.m.): 1.20(d,4xCH$_3$)6.8–8.0(m,2xC$_6$H$_4$) 10.0(s,NH).

(7) 1[4(p-butyloxybenzamide)phenoxy]-3-isopropylamine-2-propanol
(Form.I R=CH(CH$_3$)$_2$ R$_1$=4-OC$_4$H$_9$).
m.p. 152°–154° C.
I.R. (nujol) $\nu$ (cm$^{-1}$): 1635 (CO).
H-NMR(DMSO) $\delta$ (p.p.m.): 1.05(t, CH$_3$)1.10(d,2xCH$_3$) 1.3–2.0(m,2xCH$_2$)2.7–3.1 (m,CH$_2$+CH) 3.6–4.2 m,CH$_2$+CH)6.8–8.1 (m,2xC$_6$H$_4$) 10.0(s,NH).

(8) 1-isopropylamine-3-[4(p-pentyloxybenzamide)-phenoxy]-2-propanol
(Form.I R=CH(CH$_3$)$_2$ R$_1$=4-OC$_5$H$_{11}$).
m.p. 157°–159° C.
I.R. (nujol) $\nu$ (cm$^{-1}$): 1635 (CO).
H-NMR(DMSO) $\delta$ (p.p.m.): 0.95(t, CH$_3$)1.0(d,2xCH$_3$) 1.2–2.0(m,3xCH$_2$)2.6–3.0 (m,CH$_2$+CH) 3.8–4.3(m,CH$_2$+CH)6.9–8.05 (m,2xC$_6$H$_4$)10.0(s,NH).

(9) 1[4(p-hexyloxybenzamide)phenoxy]-3-isopropylamine-2-propanol hydrochloride
(Form.I R=CH(CH$_3$)$_2$HCl R$_1$=4-OC$_6$H$_{13}$).
m.p. 199°–201° C.
I.R. (nujol) $\nu$ (cm$^{-1}$): 1635 (CO).
H-NMR(DMSO) $\delta$ (p.p.m.): 0.8(t,CH$_3$)1.10(d,2xCH$_3$) 1.3–1.9(m,4xCH$_2$)2.9–3.6 (m,CH$_2$+CH)3.6–4.5(m,CH$_2$+CH) 6.8–8.2 (m,2xC$_6$H$_4$)10.1(s,NH).

(10) 1-isopropylamine-3-[4(p-octyloxybenzamide)-phenoxy]-2-propanol
(Form.I R=CH(CH$_3$)$_2$ R$_1$=4-OC$_8$H$_{17}$).
m.p. 116°-118° C.
I.R. (nujol) $\nu$ (cm$^{-1}$): 1645 (CO).
(11) 1[4(p-benzyloxybenzamide)phenoxy]-3-isopropylamine-2-propanol hydrochloride
(Form.I R=CH(CH$_3$)$_2$HCl R$_1$=4OCH$_2$-C$_6$H$_5$).
m.p. 217°-220° C.
I.R. (nujol) $\nu$ (cm$^{-1}$): 1645 (CO).
H-NMR(DMSO) $\delta$ (p.p.m.): 1.3(d,2xCH$_3$)2.8–3.2 (m,CH$_2$+CH) 3.8–4.4(m,CH$_2$+CH)5.2(s,CH$_2$) 6.85–7.10(m,2xC$_6$H$_4$+C$_6$H$_5$).

Non-limitative examples of pharmaceutically acceptable non-toxic salts of the compounds above mentioned are: chloride, bromide, iodide, phosphate, sulfate, tartrate, and citrate, as well as methyliodide, methylbromide, ethylbromide, and ethyliodide. The optical isomers of the compounds of general formula I are also included in the present invention.

Another object of the present invention is to provide the compounds having general formula II to be used as intermediate compounds for preparing the derivatives of general formula I:

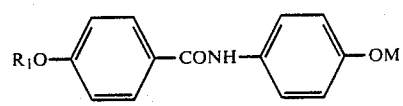

II

| R$_1$ | CONH position | m.p. (°C.) |
|---|---|---|
| 4-CH$_3$ | 4 | 236–8 |
| 4-C$_2$H$_5$ | 4 | 235–7 |
| 4-C$_3$H$_7$ | 4 | 223–5 |
| 4-isoC$_3$H$_7$ | 4 | 213–5 |
| 4-C$_4$H$_9$ | 4 | 217–20 |
| 4-C$_5$H$_{11}$ | 4 | 216–17 |
| 4-C$_6$H$_{13}$ | 4 | 205–7 |
| 4-C$_6$H$_5$CH$_2$ | 4 | 242–44 |

It is a further object of this invention to provide processes for preparing the products of general formulae I and II.

The compounds of general formula I can be prepared by starting from a compound of formula:

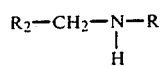

where R$_1$ has the same meaning as in formula I, and M is a hydrogen atom or an alkali metal and reacting it with a compound of formula:

R$_2$—CH$_2$—N—R
            |
            H

III where R has the same meaning as in formula I, and R$_2$ is a group

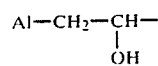

or a group

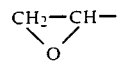

where Al is a halogen atom. The reaction is preferably carried out in a solvent such as alcohol, dioxane, dimethylformamide, and water.

The compounds of general formula II can be obtained, for example, by starting from the chloride of the appropriate benzoic acid and aminophenol.

The compounds of formula III can be prepared for example by starting from a 1,3-dihalogen-2-propanol or from epihalogenhydrin with an amine having the formula

RNH$_2$ where R has the same meaning as in formula I.

The compounds of general formula I can also be prepared by reacting a compound of the formula

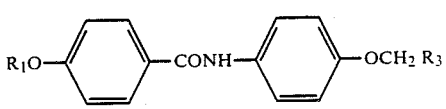

IV where R$_1$ has the same meaning as in formula I and R$_3$ is a group

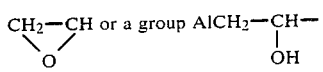

where Al is a halogen atom, with an amine having the formula: NH$_2$R where R is defined as in formula I. In this reaction the solvent to be used is either an amine excess or a preferably polar solvent, as for example ethanol.

The halogenhydrin of formula IV can be obtained by reacting a compound of formula II with epihalogenhydrin as for example epihalogenhydrin. The epoxide of formula IV can be obtained through conventional methods, for example, by the already cited halogenhydrin with sodium hydrate.

The compounds of formula I can also be obtained through the reduction of a compound having the formula

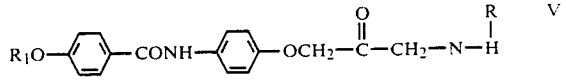

V where R and R$_1$ are defined as in formula I.

The reduction of the compound V is preferably carried out with hydride, as for example sodium boron hydride.

The compounds of formula V can be obtained by starting from compounds of formula II with 1,3 dihalogenacetone, as for example 1,3-dichloroacetone, through the corresponding compound

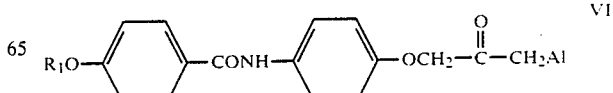

VI and subsequent treatment with an amine of the formula $RNH_2$ where R is defined as in formula I.

The present invention has the further object to provide a process for preparing optical isomers, according to the classical techniques used to separate said isomers from the racemic forms.

For example, the compound in racemic form can be reacted with an optically active acid, followed by fractionated crystallization of the diastereoisomers mixture obtained with a suitable solvent, such as for example ethanol, and then the optically active derivative is freed from the salt by treatment with a base.

The present invention has also the object to provide a process for preparing the esters derived by starting from compounds of formula I and following the classical methods of treating, for example, with anhydride or acid chloride.

The derivatives of general formula I, as well as the corresponding esters, can be transformed into addition salts of acids or of alkylhalides through the conventional methods.

The invention has also the object to provide pharmaceutical compositions including, as active ingredient, one or more derivatives according to the general formula I (or esters, or addition salts) in association with a pharmaceutically acceptable diluent or carrier.

As appropriate compositions, there may be mentioned for instance, tablets, capsules, aqueous or oily solutions or suspensions, emulsions, or dispersing powders, pulverizing or aerosol compositions, e.g. in a suitable form for oral, parenteral or rectal administration.

The invention is illustrated but not limited by the following examples:

EXAMPLE 1

1-isopropylamine-3[4(p-methoxybenzamide)phenoxy]-2-propanol 0.02 mol of 4(p-methoxybenzamide)phenol are put into 120 ml of a 0.02N potassium hydrate aqueous solution, then 0.045 mol of epichlorohydrin are added in 10 ml methanol and the mixture is kept stirring at room temperature for two days.

The reaction product is filtered out, washed twice with water (50 ml), then the resulting crude epoxide is suspended in methanol (300 ml), to which water (0.5 ml) and isopropylamine (0.6 mol) are added. After stirring for two days at room temperature, the reaction product is filtered out, vacuum dried, and added to some water again.

The reaction product, once crystallized, yields the corresponding n-propanol m.p. 174°–176° C.

This product, dissolved into ether over anhydrous gaseous hydrochloric acid yields the hydrochloride (ethyl alcohol) m.p. 192°–194° C.

EXAMPLE 2

1-terbutylamine-3[4(p-methoxybenzamide)phenoxy]-2-propanol

To 0.028 mol of crude 1-[4(p-methoxybenzamide)-phenoxy]-2,3-epoxypropane, obtained as in example 1, and suspended in methanol (300 ml), water (0.5 ml) and ter-butylamine (0.6 mol) are added. After stirring for 48 h at room temperature, the reaction product is filtered out, vacuum dried, taken up with acetone (20 ml) and subjected to gaseous hydrochloric acid; the precipitate thus obtained is filtered out and dissolved in water, and through alkalinization there is obtained a precipitate which is filtered, washed and dried; the latter, once dissolved in acetone and subjected to gaseous HCl, yields the corresponding hydrochloride (dioxane/isopropanol) (m.p. 210°–212° C.).

EXAMPLE 3

1[4(p-butyloxybenzamide)phenoxy]-3-isopropylamine-2-propanol 0.08 mol of 4(p-butyloxybenzamide)phenol are heated for 6 h over b.m. in epichlorohydrin (0.64 mol) and piperidine (0.1 ml). The epichlorohydrin excess is distilled, then the residue is taken up with ether and filtered to the pump.

The crude product 1[4(p-butyloxybenzamide)-phenoxy]-3-chlorine-2-propanol thus obtained is suspended in methanol (600 ml); after addition of isopropylamine (1.8 mol), the product is stirred at room temperature for 48 hours and then filtered out. The filtrate is dried, taken up with acetone (15 ml), filtered and crystallized from ethanol: m.p. 152°–154° C.

EXAMPLE 4

1[4(p-allyloxybenzamide)phenoxy]-3-isopropylamine-2-propanol 0.08 mol of 4(p-allyloxybenzamide)phenol are heated for 6 h over b.m. in epichlorohydrin (0.64 mol) and piperidine (0.1 ml). The epichlorohydrin excess is distilled, then the residue is taken up with ether and filtered to the pump.

The crude product 1[4(p-allyloxybenzamide)phenoxy]-3-chlorine-2-propanol thus obtained is suspended in methanol (1 lt) to which isopropylamine (1.8 mol) is added. After stirring for 72 h at room temperature, the product is filtered, dried, washed with water, filtered and dried again, and then the product is taken up with acetone and subjected to anhydrous gaseous hydrochloric acid to obtain the hydrochloride crystallized from isopropanol (m.p. 200°–202° C.).

EXAMPLE 5

1[4(p-ethoxybenzamide)phenoxy]-3-isopropylamine-2-propanol 0.02 mol of 4(p-ethoxybenzamide)phenol are put into 120 ml of a potassium hydrate 0.02N aqueous solution, afterwards epichlorohydrin (0.045 mol) in methanol (10 ml) is added, followed by stirring at room temperature for 48 h. The product is filtered, washed twice with water (50 ml) and the crude 1[4(p-ethoxybenzamide)-phenoxy]-2,3-epoxypropane is suspended in methanol (200 ml), and water (0.2 ml) and isopropylamine (0.5 mol) are added.

After having stirred for two days at room temperature, the product is filtered and dried. It is dissolved in acetone and treated with anhydrous gaseous hydrochloric acid; the hydrochloride crystallized from isopropanol has a m.p. of 215°–217° C.

Biological activity

The beta-sympatholytic activity of the compounds under examination has been tested in vivo as antagonist to the $\beta_1$-chronotropic effects (cardiac frequency increase), $\beta_1$-inotropic effects (systolic ejection velocity increase), and $\beta_2$ effects (diastolic pressure lowering) of the isoprenaline upon the anaesthetized and reserpenized rat, after oral administration, and in vitro as antagonist to the $\beta_1$ chronotropic effects (cavy right atrium), $\beta_1$ inotropic effects (cavy ventricle) and $\beta_2$ effects (cavy trachea) of the isoprenaline.

Through the in vivo and in vitro results it is evident that the 1-alkylamine-3[4(p-alkyloxybenzamide)-phenoxy]-2-propanol derivatives, which are the object of the present invention, show $\beta$-blocking activity of a competitive type and, contrary to $\beta$-blocking constituents such as propranolol, they show cardioselectivity and inherent sympathicomimetic activity, the latter being revealed by the relevant increase of the cardiac frequency in the reserpenized animal at rest.

The beta-sympatholytic activity of the 1-alkylamine-3[4(p-alkyloxybenzamide)phenoxy]-2-propanol compounds is in vivo significantly greater than the compounds such as propranolol which, although more active in vitro, are subjected to a relevant decrease of the in vivo activity owing to an intense liver metabolism. All these favourable characteristics, that is, cardioselectivity, inherent sympathicomimetic activity and lack of a significant power gap between vivo and vitro are also present in the 4-benzamide (or acetamide)phenoxy-3-isopropylamine-2-propanol derivatives, such as for example 1-(4-benzamide phenoxy)-3-isopropylamine-2-propanol (Ralph Howe and Leslie Harold Smith, U.S. 3,408,387; A. F. Crowther, R. Howe and L. H. Smith, J. Med. Chem. 14 (6), 511, 1971), 1[4(-p-chlorobenzamide)phenoxy]-3-isopropylamine-2-propanol (A. F. Crowther, R. Howe and L. M. Smith, J. Med. Chem. 14, (6), 511, 1971), and practolol (Howe and Smith, U.S. 3,408,387; Scales and Cosgrove, J. Pharmacol. Exp. Ther. 175, 338, 1970). On the other hand, compared to the latter compounds, the 1[4(p-alkyloxybenzamide)-phenoxy]-3-isopropylamine-2-propanol derivatives present also a new pharmacological characteristic, namely a significantly greater power to block the $\beta_1$ chronotropic effects with respect to the $\beta_1$ inotropic effects of the isoprenaline. The in vivo tests have shown that at certain dosage levels the compounds of this invention determine a significant beta-sympatholytic effect on the cardiac frequency (chronotropism) without a concurrent reduction of the myocardium contractility (inotropism).

Since the antianginal activity of the beta-sympatholytic agents is performed through the reduction of the cardiac frequency (Bardaux, A. et Eur. J. Pharmacol. 39, 287, 1966; Gross, G. J. and Waltier, Dc., J. Pharm. Exp. Ther. 203, 544, 1977) the 1[4(p-alkyloxybenzamide)phenoxy]-3-isopropylamine-2-propanol derivatives should carry out, as compared to the beta-blocking agents of current use in therapy, a significant anti-ischemic action with a very minor risk of determining a hypocinetic condition of the myocardium which, in turn, is considered a decisive element for the appearance of angor crysis (Kaverina, N. V. and Chumburidze, V. B., Pharmac. Ther. 4, 109, 1979).

It is also interesting to note that the 1[4(p-alkyloxybenzamide . . . or 1[4(m-alkyloxybenzamide) phenoxy]-3-isopropylamine-2-propanol derivatives, as well as the 1[2(p-alkyloxybenzamide . . . or 1[3(p-alkyloxybenzamide)phenoxy]-3-isopropylamine-2-propanol derivatives, although endowed with $\beta$-sympatholytic activity of a competitive type, with cardioselectivity, and with inherent sympathicomimetic activity, present a minor activity as compared to the corresponding derivatives of the present invention, and in some cases they are lacking in chronotropic activity.

From these results will be apparent the fundamental importance of the full replacement of the phenoxy group with a p-alkyloxybenzamide group.

The replacement of an alkyloxy group with another group will determine either a distinct reduction of activity or a loss of selectivity; a reduction of activity or a loss of selectivity will occur also by introducing more alkoxyl groups.

Hence, the present invention also contemplates a method of medicinally treating difficulties or effects induced by hyperactivity of the sympathetic nervous system in a subject, to provide improved beta-sympatholytic activity including, besides $\beta_1$-cardioselectivity, intrinsic sympathicomimetic activity and high biodisposability, also high chronotropic selectivity, and especially for blocking beta chronotropic effects, which comprises administering to such a subject an effective $\beta_1$-cardioselective, intrinsic sympathiocometically active, biodisposable and/or beta chronotropic blocker, amount of a compound of formula I above, i.e. a 1-alkylamino-3-[4-(p-alkyloxybenzamido)phenoxy]-propan-2-ol, or a corresponding pharmaceutically acceptable non-toxic salt thereof, optionally in the form of a composition with said compound or salt being present as active principle in association with a pharmaceutically acceptable carrier.

We claim:

1. A derivative of 1-alkylamine-3-[4(p-alkyloxybenzamide)phenoxy]-2-propanol of general forumla I and the pharmaceutically acceptable, non-toxic salts thereof:

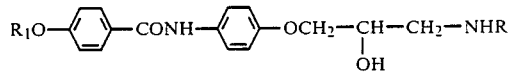

where $R_1$ is a linear or branched alkyl chain with 1 to 8 carbon atoms included, an alkenyl chain with 2 to 8 carbon atoms included, or an arylalkyl chain with 7 to 10 carbon atoms included, and R is a linear or branched alkyl group with 1 to 8 carbon atoms included.

2. A compound as claimed in claim 1, in optically active form.

3. Pharmaceutically acceptable, non toxic salts of compounds according to claim 1.

4. Pharmaceutically acceptable, non toxic salts of compounds according to claim 2.

5. A compound according to claim 1, selected from the group consisting of 1-isopropylamino 3[4(p-methoxybenzamide)phenoxy]-2-propanol and a pharmaceutically acceptable salt thereof, 1-t-butylamino-3[4(p-methoxybenzamido)phenoxy]-2-propanol and a pharmaceutically acceptable salt thereof, 1[4(p-ethoxybenzamido)phenoxy]-3-isopropylamino-2-propanol and a pharmaceutically acceptable salt thereof, 1[4(p-allyloxybenzamido)phenoxy]-3-isopropylamino-2-propanol and a pharmaceutically acceptable salt thereof, 1-isopropylamino-3[4(p-propyloxybenzamido)phenoxy]-2-propanol and a pharmaceutically acceptable salt thereof, 1-isopropylamino-3[4(p-isopropyloxybenzamido)phenoxy]-2-propanol and a pharmaceutically acceptable salt thereof, 1[4(p-butyloxybenzamido)phenoxy]-3-isopropylamino-2-propanol and a pharmaceutically acceptable salt thereof, 1-isopropylamino-3[4(p-pentyloxybenzamido)phenoxy]-2-propanol and a pharmaceutically acceptable salt thereof, 1[4(p-hexyloxybenzamido)phenoxy]-3-isopropylamino-2- propanol and a pharmaceutically acceptable salt thereof, 1-isopropylamino-3[4(p-octyloxybenzamido)phenoxy]-2-propanol and a pharmaceutically acceptable salt thereof, 1[4(p-benzyloxybenzamido)phenoxy]-3-isopropylamino-2-propanol and a pharmaceutically acceptable salt thereof.

6. A compound of claim 1 wherein $R_1$ is a linear or branched alkyl chain with 1 to 8 carbon atoms included.

7. A compound of claim 1 wherein $R_1$ is an alkenyl chain with 2 to 8 carbon atoms included.

8. A compound of claim 1 wherein $R_1$ is an arylalkyl chain with 7 to 10 carbon atoms included.

9. A pharmaceutical composition comprising an effective beta chronotropic-blocker amount of at least one compound of claim 1 as active principle in association with a pharmaceutically acceptable carrier.

10. Composition of claim 9 in a suitable form for oral, parenteral or rectal administration.

11. Pharmaceutical composition comprising an effective beta chronotropic-blocker amount of a compound selected from the group consisting of a derivative of 1-alkylamino-3-[4-(p-alkyloxybenzamido)phenoxy]-propan-2-ol of the formula

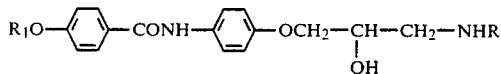

wherein $R_1$ is a linear or branched alkyl chain having 1 to 8 carbon atoms inclusive, an alkenyl chain having 2 to 8 carbon atoms inclusive, or an arylalkyl chain having 7 to 10 carbon atoms inclusive, and R is a linear or branched alkyl group having 1 to 8 carbon atoms inclusive, and the pharmaceutically acceptable non-toxic salts thereof, as active principle in association with a pharmaceutically acceptable carrier.

12. Composition of claim 11 wherein said compound is in optically active form.

13. Composition of claim 11 in a suitable form for oral, parenteral or rectal administration.

14. Composition of claim 11 wherein $R_1$ is a linear or branched alkyl chain having 1 to 8 carbon atoms inclusive.

15. Composition of claim 11 wherein $R_1$ is an alkenyl chain having 2 to 8 carbon atoms inclusive.

16. Composition of claim 11 wherein $R_1$ is an arylalkyl chain having 7 to 10 carbon atoms inclusive.

17. Method of treating beta chronotropic effects induced by hyperactivity of the sympathetic nervous system in a subject for blocking such beta chronotropic effects, which comprises administering to such a subject an effective beta chronotropic-blocker amount of a compound selected from the group consisting of a derivative of 1-alkylamino-3-[4-(p-alkyloxybenzamido)phenoxy]-propan-2-ol of the formula

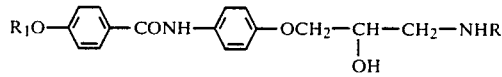

wherein $R_1$ is a linear or branched alkyl chain having 1 to 8 carbon atoms inclusive, an alkenyl chain having 2 to 8 carbon atoms inclusive, or an arylalkyl chain having 7 to 10 carbon atoms inclusive, and R is a linear or branched alkyl group having 1 to 8 carbon atoms inclusive, and the pharmaceutically acceptable non-toxic salts thereof.

18. Method of claim 17 wherein said compound is in optically active form.

19. Method of claim 17 wherein said compound is in the form of composition comprising an effective beta chronotropic-blocker amount of said compound as active principle in association with a pharmaceutically acceptable carrier.

20. Method of claim 17 wherein said compound is selected from the group consisting of 1-isopropylamino-3-[4-(p-methoxybenzamido)phenoxyl]-propan-2-ol; 1-t-butylamino-3-]4-(p-methoxybenzamido)phenoxy]-propan-2-ol; 1-[4-(p-ethoxybenzamido)phenoxy]-3-isopropylamino-propan-2-ol; 1-[4-(p-allyloxybenzamido)phenoxy]-3-isopropylamino-propan-2-ol; 1-isopropylamino-3-[4-(p-propyloxybenzamido)phenoxy]-propan-2-ol; 1-isopropylamino-3-[4-(p-isopropyloxybenzamido)phenoxy]-propan-2-ol; 1-[4-(p-butyloxybenzamido)phenoxy]-3-isopropylamino-propan-2-ol; 1-isopropylamino-3-[4-(p-pentyloxybenzamido)phenoxyl]-propan-2-ol; 1-[4-(p-hexyloxybenzamido)phenoxy]-3-isopropylamino-propan-2-ol; 1-isopropylamino-3-[4-(p-octyloxybenzamido)phenoxy]-propan-2-ol; 1-[4-(p-benzyloxybenzamido)phenoxy]-3-isopropylamino-propan-2-ol; and the corresponding pharmaceutically acceptable salts thereof.

* * * * *